(12) United States Patent
He

(10) Patent No.: US 11,224,439 B2
(45) Date of Patent: Jan. 18, 2022

(54) HEMOSTATIC CLIP DEVICE

(71) Applicant: SHANGHAI AIERDUN MEDICAL INSTRUMENT CO., LTD., Shanghai (CN)

(72) Inventor: Changhui He, Shanghai (CN)

(73) Assignee: SHANGHAI AIERDUN MEDICAL INSTRUMENT CO., LTD., Shanghai (CN)

( * ) Notice: Subject to any disclaimer, the term of this patent is extended or adjusted under 35 U.S.C. 154(b) by 152 days.

(21) Appl. No.: 16/509,490

(22) Filed: Jul. 11, 2019

(65) Prior Publication Data

US 2019/0336130 A1 Nov. 7, 2019

Related U.S. Application Data

(63) Continuation-in-part of application No. PCT/CN2017/080620, filed on Apr. 14, 2017.

(30) Foreign Application Priority Data

Feb. 24, 2017 (CN) .......................... 201710102621.4

(51) Int. Cl.
*A61B 17/122* (2006.01)
*A61B 17/29* (2006.01)
*A61B 17/12* (2006.01)

(52) U.S. Cl.
CPC ............ *A61B 17/122* (2013.01); *A61B 17/29* (2013.01); *A61B 2017/12004* (2013.01); *A61B 2017/2946* (2013.01)

(58) Field of Classification Search
CPC ... A61B 17/122; A61B 17/1285; A61B 17/29; A61B 2017/12004; A61B 2017/2931;
(Continued)

(56) References Cited

U.S. PATENT DOCUMENTS

2016/0367258 A1* 12/2016 Jin ..................... A61B 17/1285
2017/0202576 A1* 7/2017 Zeng ................... A61M 25/005

FOREIGN PATENT DOCUMENTS

CN         103989500 B    11/2015
CN         105935304 A     9/2016
(Continued)

OTHER PUBLICATIONS

The extended European Search Report of counterpart European Patent Application No. 17897870.6 dated Oct. 30, 2020.

*Primary Examiner* — Brooke Nicole Labranche

(57) ABSTRACT

The present invention relates to a medical instrument, and particularly relates to a hemostatic clip device. The device includes a clamping component and a holder component. The head portion of the sleeve is provided with open slots for clamping arms to move. The tail ends of the outer side edges of clamping arms each is provided with a recess. A hole, corresponding to the position of the recess of one clamping arm, is formed in the other one. The sleeve is connected with the sleeve holder through inner core. The head end of the double-wire supporting arm is connected with the holes, and the other end is connected with wire rope and passes through the sleeve, the inner core, the sleeve holder and a bourdon tube so as to be connected with an operation handle. The device has the advantages of simple structure, firm clamping, convenient use and the like.

4 Claims, 5 Drawing Sheets

(58) Field of Classification Search
CPC .... A61B 2017/2934; A61B 2017/2936; A61B 2017/2937; A61B 2017/2945; A61B 2017/2946; A61B 17/128; A61B 17/12; A61B 17/12013
See application file for complete search history.

(56) References Cited

FOREIGN PATENT DOCUMENTS

| | | |
|---|---|---|
| CN | 106236182 A | 12/2016 |
| EP | 3081174 A1 | 10/2016 |

* cited by examiner

HEMOSTATIC CLIP DEVICE

CROSS REFERENCE TO RELATED APPLICATIONS

The present application is a Continuation-In-Part Application of PCT Application No. PCT/CN2017/080620 filed on Apr. 14, 2017, which claims the benefit of Chinese Patent Application No. 201710102621.4 filed on Feb. 24, 2017. All the above are hereby incorporated by reference.

TECHNICAL FIELD

The present invention relates to a medical instrument used inside a human body, and more particularly relates to a hemostatic clip device applied to a soft endoscope and convenient for separation operation.

BACKGROUND ART

The invention patent No. ZL201410222753.7 discloses a hemostatic clip which is widely applied to clinical surgery due to its high hemostasis efficiency, small wound surface and few complications. The opening of clamping arms of the invention patent depends on two sliding chutes in the middles of the clamping arms, one movable pin shaft and one fixed pin shaft. The two sliding chutes are respectively located in the middles of the clamping arms, and are divided into arc-shaped sliding sections and locking sections. The two arc-shaped sliding sections are disposed in a crossed mode. Before the hemostatic clip of this invention is used, the clamping arms are in a closed state, and at the moment, the pin shaft is located at the tail portions of the arc-shaped sliding sections of the two sliding chutes and does not enter the locking sections. When the hemostatic clip is used, the pin shaft forces the clamping arms to open under the action of a pushing force. After the hemostatic clip is used, the clamping arms are in a closed and locked state, and at the moment, the clamping arms are pulled back, and the pin shaft forces the lengthened arms to be closed. When a pulling force reaches a critical value, the pin shaft enters the locking sections of the sliding chutes, and the clamping arms are dead locked, and a steel wire mouth falls off. However, the hemostatic clip of this invention has the defects of complex structure and high production cost, and is inconvenient to use since a relatively high force is needed in the process of opening, closing and unhooking the clamping arms. Therefore, there is an urgent need for a hemostatic clip device which may reduce the cost, is simpler in structure, higher in use reliability, safe and effectively and is used cooperatively with an endoscope.

SUMMARY OF THE INVENTION

The present invention is implemented as follows. A hemostatic clip device includes a clamping component 1 and a holder component 2. The clamping component includes clamping arms, a pin and a sleeve. The head portion of the sleeve is provided with two symmetrically disposed open slots for the clamping arms to move. The holder component includes a double-wire supporting arm, a fixing ring and a sleeve holder. Each of the tail ends of the outer side edges of the two symmetrically disposed clamping arms is provided with a recess. A hole, corresponding to the position of the recess of one clamping arm, is formed on the other clamping arm. The sleeve is connected with the sleeve holder through an inner core. The head end of the double-wire supporting arm is connected with the holes, and the other end of the double-wire supporting arm is connected with a wire rope and passes through the sleeve, the inner core, the sleeve holder and a bourdon tube so as to be fixedly connected with a handle at an operation end. The bourdon tube is fixedly connected with the tail portion of the sleeve holder. When the clamping arms are in a closed state, the pin is located at the root portion (namely the last end position) of a travel of an "L"-shaped locking slot, and the tail portions of the clamping arms are overlapped and located in the open slots of the sleeve.

When the double-wire supporting arm is pushed, the two clamping arms are in an opening process: the tail portions of the clamping arms are expanded outwards in the open slots of the sleeve, and at the moment, the pin is located at the root portion of the "L"-shaped locking slot.

When the double-wire supporting arm is pulled, the two clamping arms are in a closing process: the tail portions of the clamping arms are contracted in the open slots of the sleeve, and at the moment, the pin is still located at the root portion of the "L"-shaped locking slot.

When the double-wire supporting arm is continuously pulled, the pin moves forwards in the "L"-shaped locking slot until the top end of the locking slot, and at the moment, the clamping arms are locked.

When the double-wire supporting arm is further pulled, an overlapped portion of the tail portions of the clamping arms is inserted into an inner hole of the sleeve, and at the moment, the clamping arms are double locked.

If the double-wire supporting arm is continuously pulled, the double-wire supporting arm falls off from the holes, and then the inner core falls off from the sleeve.

The inner hole in the middle of the sleeve is provided with a convex ring. When the tail portions of the clamping arms are pulled into the inner hole, provided with the convex ring, in the middle of the sleeve, the clamping arms are ensured to be stable in a locked state and not to be suddenly released.

The tail end of the inner core is in nested connection with the sleeve holder, and the head end of the inner core is provided with at least two leaf springs in inserted connection with the sleeve.

The double-wire supporting arm is of a Y-shaped structure. The fixing ring is disposed at a position, located on the tail end portion of the inner core, on the double-wire supporting arm and is configured for pulling out the connection between the inner core and the sleeve.

The inner core is composed of an inner core holder and the leaf springs. The at least two leaf springs are fixed at the front end of the inner core holder. The tail end of the inner core holder is provided with a small hole through which the double-wire supporting arm passes.

The present invention has the advantages that: the clamping arms totally have three working processes: opening, closing and locking; and since the two clamping arms rotate by taking the root portion of the locking slot as a circle center in the opening and closing processes of the clamping arms, and the locking slot is at an overlapped position in the locking process, the pin may be moved to the top end of the locking slot only by a pretty small pulling force. Therefore, the present invention has the advantages of simple structure, smooth pulling and pushing, easy and convenient opening and closing, easy unhooking, firm clamping, convenient use and the like.

DETAILED DESCRIPTION OF THE INVENTION

Figure 1:
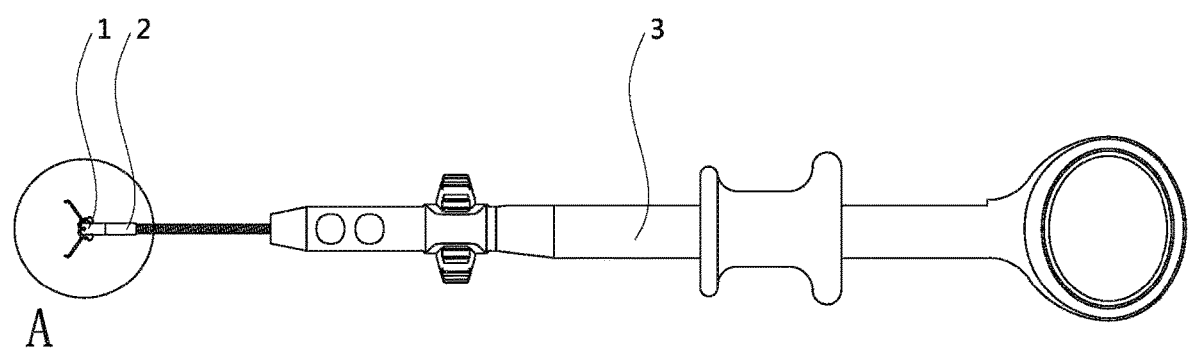
FIG. 1 is an overall structural schematic diagram of the present invention, wherein the portion A includes a clamping component 1 and a holder component 2.

A hemostatic clip device of the present invention is used in surgery. The clip device is adopted to clamp a tissue for hemostasis. A specific embodiment of the hemostatic clip device of the present invention is composed of a clamping component 1, a holder component 2 and an operation handle 3. In FIG. 1, A includes the clamping component 1 and the holder component 2. The operation handle 3 drives a wire rope to pull a double-wire supporting arm 21 to control the opening and closing of the clip device with the sliding of a handle ring. By rotating a rotating shaft, an opening direction of the hemostatic clip device may be controlled. The handle ring is pushed to open the hemostatic clip device with a maximum opening angle of 110 degrees, which may clamp a wide range of tissues.

Figure 2:
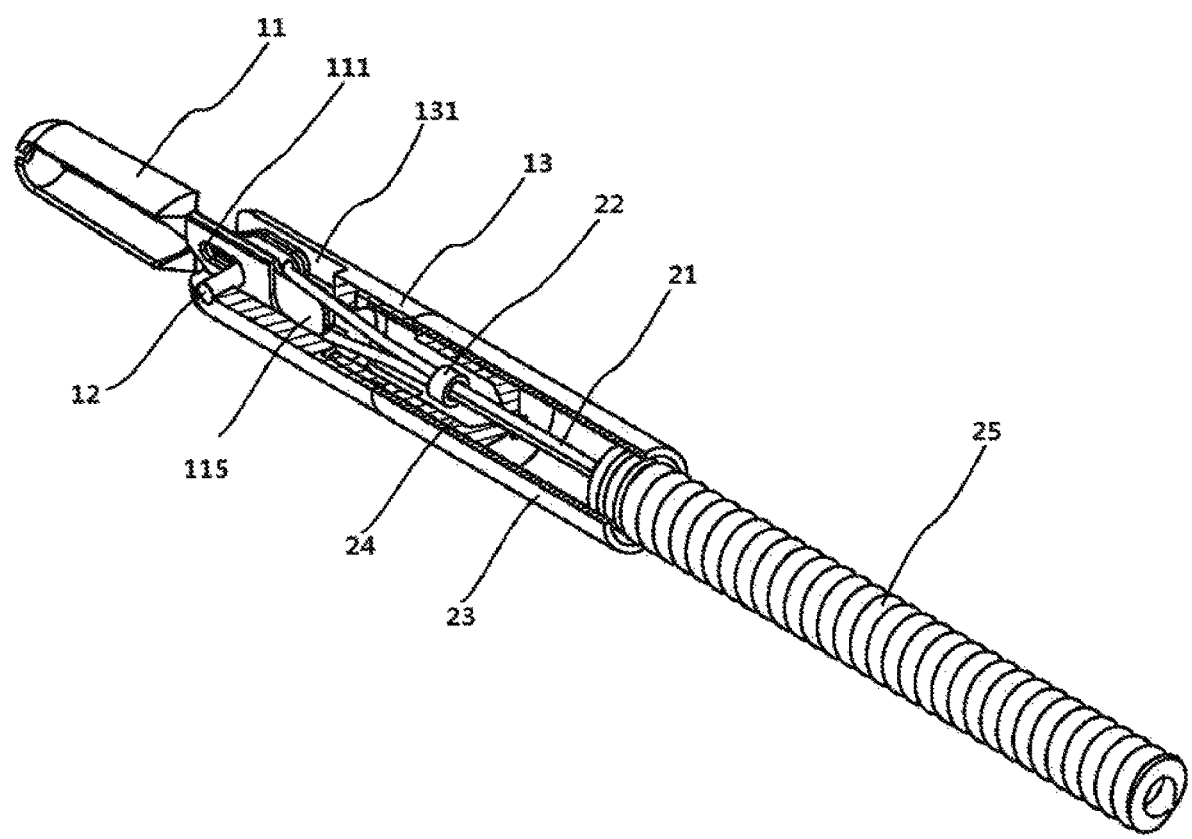
FIG. 2 is a structural schematic diagram of the portion A of the present invention.
Figure 5:
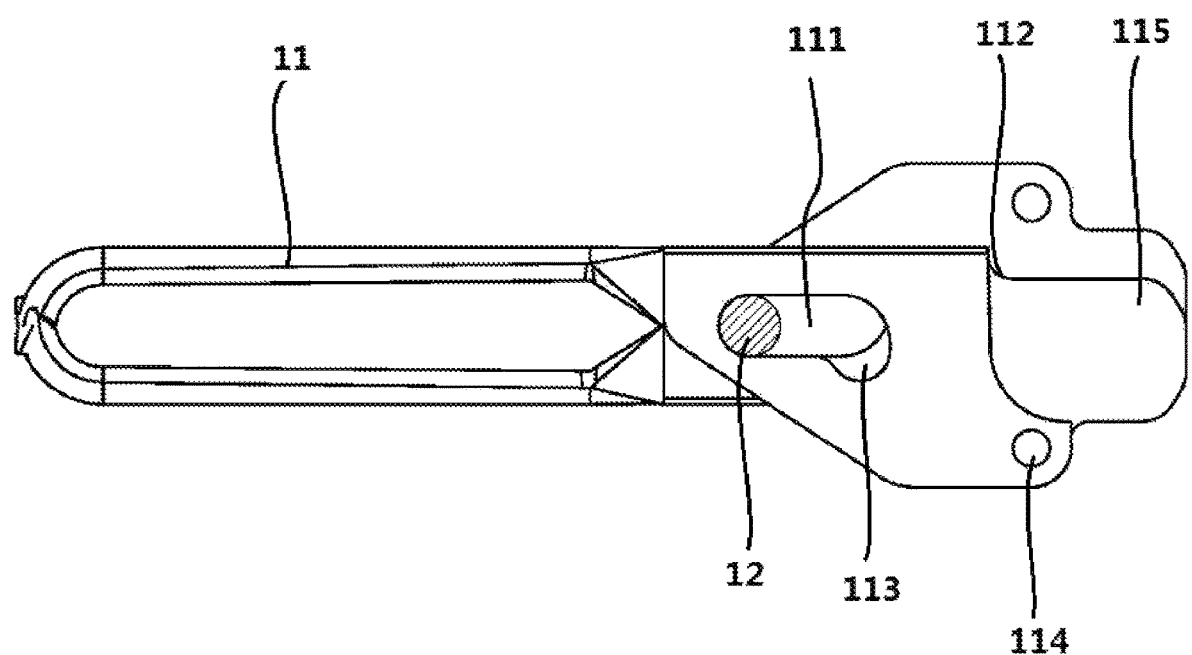
FIG. 5 is a structural schematic diagram of the locked clamping arms of the front-end structure of the present invention.

Referring to FIG. 1 and FIG. 2, the clamping component 1 is composed of a pair of clamping arms 11, a pin 12 and a sleeve 13. The head portion of the sleeve 13 is provided with two symmetrically disposed open slots 131. The open slots 131 provide a space for opening and closing movement of the clamping arms 11. The holder component 2 is composed of a double-wire supporting arm 21, a fixing ring 22, a sleeve holder 23, an inner core 24 and a bourdon tube 25. The sleeve 13 is connected with the sleeve holder 23 through the inner core 24. The bourdon tube 25 is fixedly connected with the tail portion of the sleeve holder 23. Each of the tail ends of the outer side edges of the two symmetrically disposed clamping arms 11 is provided with a recess 112. Referring to FIG. 2 and FIG. 5, a hole 114, corresponding to the position of the recess 112 of one clamping arm 11, is formed on the other clamping arm 11. The head end of the double-wire supporting arm 21 is connected with the holes 114 in the clamping arms 11, and the connection may be separated under the action of a pulling force. The other end of the double-wire supporting arm 21 is connected with the wire rope and passes through the sleeve 13, the inner core 24, the sleeve holder 23 and the bourdon tube 25 through the wire rope so as to be fixedly connected with the operation handle.

The inner hole in the middle of the sleeve 13 is provided with a convex ring 132. When the tail portions 115 of the clamping arms 11 are pulled into the convex ring 132 in the middle of the sleeve 12, the clamping arms 11 are ensured to be stable in a locked state and not to be suddenly released.

Figure 3:
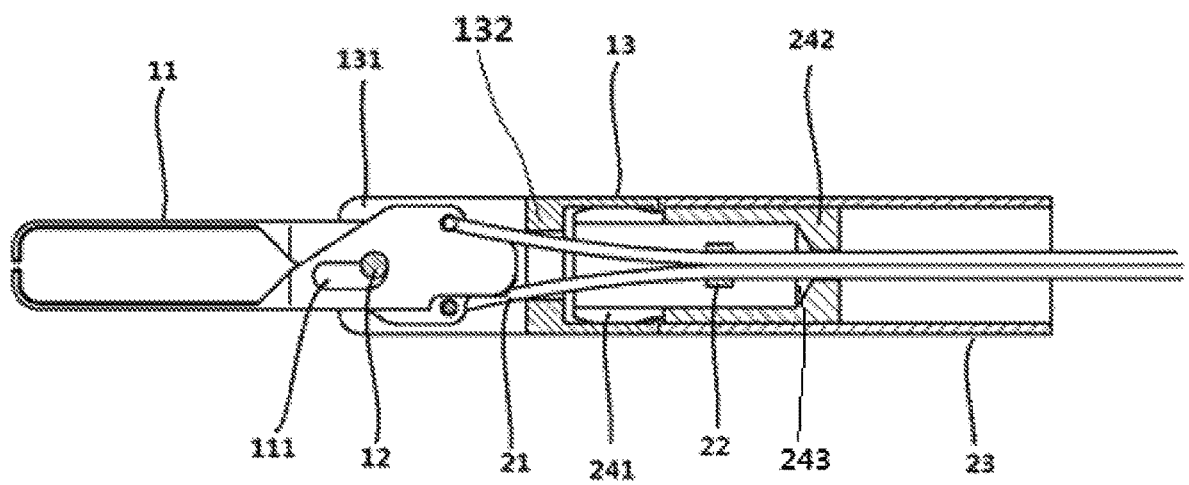
FIG. 3 is a structural schematic diagram of closing of clamping arms of a front-end structure of the present invention.

Referring to FIG. 2 and FIG. 3, a tail end inner core holder 242 of the inner core 24 is fixedly connected with the sleeve holder 23, and the head end of the inner core 24 is provided with at least two leaf springs 241 in inserted connection with the sleeve 13.

The double-wire supporting arm 21 is of a Y-shaped structure. The fixing ring 22 is disposed at a position, located on the tail end portion of the inner core 24, on the double-wire supporting arm 21 and is configured for pulling out the connection between the inner core 24 and the sleeve 13. The double-wire supporting arm 21 adopting the Y-shaped structure of the present invention is characterized in that the extension angle is larger, an opening of the hemostatic clip device is large, the maximum angle reaches 110 degrees, and more tissues are clamped.

The inner core 24 is composed of the inner core holder 242 and the leaf springs 241. The at least two leaf springs 241 are fixed at the front end of the inner core holder 242. A gap is reserved between the two leaf springs 241. The middles of the leaf springs protrude outwards to form a waist drum shape, and the leaf springs may be closed under a condition of an external centripetal force to facilitate the pulling out of the clamping component 1. The tail end of the inner core holder 242 is provided with a small hole 243 through which the double-wire supporting arm 21 passes. The diameter of the small hole 243 is less than the outer diameter of the fixing ring 22. In this way, when the double-wire supporting arm 21 is pulled to move, the inner core 24 will be forced to fall off from the sleeve 13 without causing the inner core 24 and other elements to fall into a human body together. The holder component 2 may be pulled away with the handle since the rear portion of the holder component 2 is fixed on the stainless steel bourdon tube 25.

In FIG. 3, when the double-wire supporting arm 21 is not pushed, the pin 12 disposed between the front end of the sleeve 13 and a locking slot 111 in a penetrating manner is located at the root portion of the "L"-shaped locking slot 111, and at the moment, the clamping arms 11 are in a closed state, and the tail portions 115 of the clamping arms 11 are overlapped and located in the open slots 131 of the sleeve 13.

Figure 4:
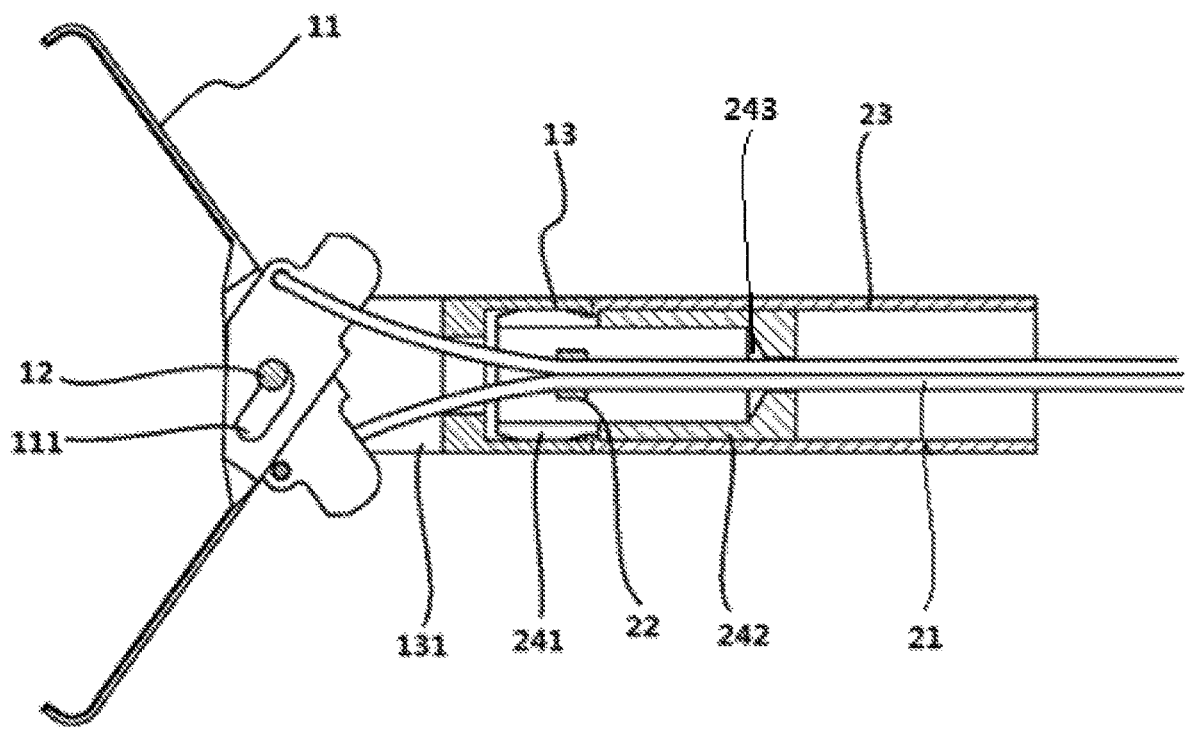
FIG. 4 is a structural schematic diagram of opening of the clamping arms of the front-end structure of the present invention.

In FIG. 4, when the double-wire supporting arm 21 is pushed, the two clamping arms 11 are in an opening process; at the moment, the tail portions of the clamping arms 11 move inside and outside the open slots 131 of the sleeve 13 till the clamping arms 11 are opened to the maximum extent, and the pin 12 is still located at the root portion 113 of the "L"-shaped locking slot 111.

When a pulling force is applied to the double-wire supporting arm 21, the two clamping arms 11 are in a closing process; at the moment, the tail portions of the clamping arms 11 move inside and outside the open slots 131 of the sleeve 13 till the clamping arms 11 are completely closed, and then the tail portions of the clamping arms 11 are overlapped; and the pin 12 is still located at the root portion 113 of the "L"-shaped locking slot 111.

Referring to FIG. 3 and FIG. 5, When a further pulling force is applied to the double-wire supporting arm 21, the pin 12 moves in the "L"-shaped locking slot 111 until the top end, and at the moment, the tail portions 115 are overlapped and inserted into the inner hole of the sleeve 13, and then the clamping arms 11 are dead locked.

The pulling force on the double-wire supporting arm 21 is continuously increased, and the double-wire supporting arm 21 falls off from the holes 114 under the resistance of the sleeve 13 to the tail portions 115 of the clamping arms 11. The clamping component 1 then clamps a tissue tight and is retained in the body, and because the clamping component 1 is separated from the holder component 2, no axially acting force exists, and the clamping component 1 is dead locked in the sleeve 13 and may not move.

What is claimed is:

1. A hemostatic clip device, comprising a clamping component and a holder component, wherein the clamping component comprises two symmetrically disposed clamping arms, a pin and a sleeve; a head portion of the sleeve is provided with two symmetrically disposed open slots for the clamping arms to move; the holder component comprises a double-wire supporting arm, a fixing ring and a sleeve holder; each of tail ends of outer side edges of the two symmetrically disposed clamping arms is provided with a recess (112); a hole, corresponding to the position of the recess, is formed on each of the clamping arms; the sleeve is connected with the sleeve holder through an inner core; the fixing ring is disposed at a position, located on a tail end portion of the inner core, on the double-wire supporting arm and is configured for pulling out a connection between the inner core and the sleeve; the double-wire supporting arm is of a Y-shaped structure; head ends of the double-wire supporting arm are respectively and directly connected with the holes, and a tail end of the double-wire supporting arm passes through the sleeve, the inner core, the sleeve holder and a bourdon tube so as to be fixedly connected with a handle at an operation end; the bourdon tube is fixedly connected with a tail portion of the sleeve holder; when the clamping arms are in a closed state, the pin is located at a root portion of a track of an "L"-shaped locking slot, and tail parts of the clamping arms are overlapped and located in the open slots of the sleeve; when the double-wire supporting arm is pushed, the two clamping arms are in an opening process: the tail parts of the clamping arms are expanded outwards in the open slots of the sleeve, and at that moment, the pin is located at the root portion of the "L"-shaped locking slot; when the double-wire supporting arm is pulled, the two clamping arms are in a closing process: the tail parts of the clamping arms are contracted in the open slots of the sleeve, and at that moment, the pin is still located at the root portion of the "L"-shaped locking slot; when the double-wire supporting arm is continuously pulled, the pin moves forward in the "L"-shaped locking slot until a top end of the locking slot, and at that moment, the clamping arms are locked; when the double-wire supporting arm is further pulled, an overlapped portion of the tail parts of the clamping arms is inserted into an inner hole of the sleeve, and at that moment, the clamping arms are double locked; and if the double-wire supporting arm is continuously pulled, the double-wire supporting arm falls off from the holes, and then the inner core falls off from the sleeve.

2. The hemostatic clip device according to claim 1, characterized in that the inner hole in a middle of the sleeve is provided with a convex ring; and when the tail parts of the clamping arms are pulled into the inner hole, provided with the convex ring, in the middle of the sleeve, the clamping arms are ensured to be stable in a locked state and not to be released.

3. The hemostatic clip device according to claim 1, characterized in that a tail end inner core holder of the inner core is fixedly connected with the sleeve holder, and a head end of the inner core is provided with at least two leaf springs in inserted connection with the sleeve.

4. The hemostatic clip device according to claim 3, characterized in that the inner core is composed of the inner core holder and the at least two leaf springs; the at least two leaf springs are fixed at the front end of the inner core holder; and a tail end of the inner core holder is provided with a small hole through which the double-wire supporting arm passes.

* * * * *